United States Patent [19]

Eckles et al.

[11] 4,326,940

[45] Apr. 27, 1982

[54] AUTOMATIC ANALYZER AND CONTROL SYSTEM FOR ELECTROPLATING BATHS

[75] Inventors: William E. Eckles; Craig V. Bishop; Peter T. Vaitekunas, all of Cleveland, Ohio

[73] Assignee: ROHCO Incorporated, Cleveland, Ohio

[21] Appl. No.: 40,505

[22] Filed: May 21, 1979

[51] Int. Cl.³ ............... C25D 17/00; C25D 21/14; G05B 15/00; G01N 35/00

[52] U.S. Cl. .................. 204/232; 118/688; 118/689; 204/195 R; 364/497; 364/500; 364/579; 422/62; 422/70; 422/81; 427/8; 427/345

[58] Field of Search ............ 204/1 T, 181 R, 232, 204/234, 237, 195 R; 422/62, 70, 81; 364/497, 499, 500, 579; 118/688, 689; 427/8, 345

[56] References Cited

U.S. PATENT DOCUMENTS

| | | | |
|---|---|---|---|
| 2,149,344 | 3/1939 | Hull | 204/1 T |
| 3,654,113 | 4/1972 | Bochinski | 204/1 T X |
| 3,658,676 | 4/1972 | DeVittorio et al. | 204/181 R |
| 3,901,653 | 8/1975 | Jones et al. | 422/62 X |
| 4,055,751 | 10/1977 | Bussmann et al. | 364/500 |
| 4,132,605 | 1/1979 | Tench et al. | 204/1 T |
| 4,146,437 | 3/1979 | O'Keefe | 204/1 T |
| 4,153,521 | 5/1979 | Litvak et al. | 204/1 T X |
| 4,155,978 | 5/1979 | Naono et al. | 422/64 |

Primary Examiner—G. L. Kaplan
Attorney, Agent, or Firm—Maky, Renner, Otto & Boisselle

[57] ABSTRACT

The invention provides an on-stream method and apparatus for analyzing of the concentrations of chemical components in a bath, especially in an electroplating bath, contained in one or more processing tanks. Moreover, the information obtained by such analysis of a single bath or of multiple baths may be efficiently employed to control such concentrations in the bath or respective baths, for example, by controlling the addition of one or more additives. The apparatus comprises a multi-steam sampling value and a computer for controlling the operation of said value. The computer also controls means for adding material to the baths in order to maintain the parameters thereof.

29 Claims, 3 Drawing Figures

AUTOMATIC ANALYZER AND CONTROL SYSTEM FOR ELECTROPLATING BATHS

BACKGROUND OF THE INVENTION

The present invention relates generally, as indicated, to automatic analyzing systems and, more particularly, to automatic analyzing systems for electroplating baths. Moreover, the invention relates to a method for automatic analysis, particularly of electroplating baths, and to a method and apparatus for automatic analysis and control of baths, such as electroplating baths.

In an electroplating bath or process changes ordinarily occur, for example, in the chemical balance of the bath, as electrochemical reactions occur. To help maintain the quality of the electroplated product and the efficiency of an electroplating bath, it is necessary to analyze the bath for one or more parameters. Shut down of a process or correction of the chemical composition of the bath may be based on the information obtained by such analysis.

One prior analysis technique for electroplating baths employed a Waters Associates Liquid Chromatograph into which a small quantity of liquid specimen manually taken from a bath on a daily basis was manually injected. For accuracy, though, it is desirable that the time lag between drawing a specimen and analysis thereof be minimized; however, using the manual specimen drawing and injecting technique, it is difficult both to minimize that time lag and to hold the same constant for each analysis. Moreover, the manual drawing and injecting of specimens is time consuming and expensive, especially when multiple baths must be separately analyzed on a daily basis. Although carousel-type specimen holders and delivering equipment have been available to provide multiple specimens sequentially to optical analyzing equipment, such as the mentioned liquid chromatograph, the individual specimens still must be manually drawn from respective baths and placed in the carousel which is then operated to provide semi-automatic delivery to the analyzing machine. Another disadvantage with the prior analyzing technique is the limited ability of the analyzing machine; for example, certain components of an electroplating bath may not affect the ultraviolet light of such liquid chromatograph and, thus, may defy detection or analysis thereby.

Historically the analysis of electroplating solutions has met with difficulty. Combinations of traditional chemical analysis, e.g. Peter Wolfram Wild *Modern Analysis For Electroplating*, (Finishing Publications Limited, Middlesex, U.K., 1974), and qualitative performance analysis, such as the Hull Cell, e.g. U.S. Pat. No. 2,149,344, have had to suffice. One recent innovation has been the use of cyclic stripping voltometry, e.g. U.S. Pat. No. 4,132,605 to characterize quantitatively the performance of a copper electroplating bath. Despite these methods of control and analysis it often occurs that poor plating characteristics manifest themselves over time as the solutions are used. Organic contaminants, trace metals, and oxidation or reduction products from the electrolysis of "brightening" or leveling addition agents may accumulate so as to eventually deleteriously affect performance of the electroplating solution.

In the past the use of chromatographic separation techniques that are reproducible provided proper detection is also employed may show buildup of materials not deliberately added to the electroplating solution. If correlative changes in the concentration of these non-deliberately added compounds with the change in plating performance are noted, the electroplater may be able to anticipate changes in performance before they adversely affect the quality of his work.

To provide frequent analysis, so that meaningful data may be accrued, is a primary intent of this invention.

SUMMARY OF THE INVENTION

Briefly, the invention provides an improved method and apparatus for analyzing the concentrations of chemical components in a bath, especially in an electroplating bath, contained in a processing tank. Moreover, the information obtained by such analysis of a single bath or of multiple baths may be efficiently employed to control such concentrations in the bath or respective baths, for example, by controlling the addition of one or more additives. Of course, other types of control also may be effected, such as, for example, temperature control and the like.

Thus, principal objects of the invention are to improve the accuracy and completeness and to facilitate the making of chemical analyses, especially of electroplating baths.

Other objects are to improve the accuracy, completeness and facility of control of concentrations of components and/or other properties of baths, especially of electroplating baths.

Additional objects are to improve the precision of electroplating baths and of the electroplating effected thereby.

Further objects are to provide programmability for analysis of electroplating baths, including the frequency with which such analyses are made, the duration of respective analyses, the nature of respective analyses (for example, the equipment used and/or the parameters used in equipment for making analyses), the number of baths analyzed, etc.

Still other objects are to obtain one or more of the foregoing and further objects and advantages while providing for analysis and/or control of multiple baths, especially of electroplating baths.

Still an additional object is to enable the facile and convenient use of high pressure liquid chromatography for monitoring and/or analyzing processes using continuous relatively low pressure on-stream sampling.

The foregoing and other objects and advantages of the present invention are obtained in an analyzer for liquid solutions, mixtures, and the like, and preferably for electroplating baths, comprising a supply means for supplying a sample for analysis and a detector means for detecting the concentration of at least one component in the sample. Preferably the supply means supplies a stream of liquid from an electroplating bath, and a selecting means selects a sample of this stream of liquid for analysis. Moreover, preferably the detector means includes plural detectors for detecting several components of the sample. Further, a pressurizing means may be provided for receiving a sample at relatively low pressure and for delivering such sample at relatively high pressure to the detector means for relatively high pressure analysis thereby. Also, the invention may include a controlled solvent delivery means for delivering at least two solvents selectively to transport a sample to and through the detector means. Preferably one or more portions of the analyzer is computer controlled, for example by a microprocessor type microcomputer, for accuracy, repeatability, and reliability of the analysis information. Furthermore, the analysis information may be employed in the invention to control the delivery of additives or to control another parameter of the analyzed bath or process to maintain the composition or another parameter of the same within predetermined tolerances.

These and other objects and advantages in accordance with the preferred embodiment and best mode of the present invention, moreover, are obtained by continuous on-stream sampling of one or more electroplating baths and selected analyzing of the same with the versatility of a combined detector system, especially for electroplating baths. Preferably such combination detector system employs both an electrochemical detector, such as a polarograph type device and a spectrophotometric type device, with the latter being upstream of the form so as not to affect the aliquot analyzed thereby and, therefore, the nature of the output information derived by the former.

To the accomplishment of the foregoing and related ends, the invention, then, comprises the features hereinafter fully described in the specification and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF THE DRAWINGS

In the annexed drawings:

FIG. 3 is a fragmentary schematic illustration of portions of the multiple sampling and high pressure sample introduction system of the analyzer.

DESCRIPTION OF THE PREFERRED EMBODIMENT

The analyzer of the present invention is described herein in connection with one for analyzing the concentration of components in an electroplating bath or process (used interchangeably below). However, it will be appreciated that the invention may be used to analyze other liquids. In accordance with the preferred embodiment and best mode of the invention, several electroplating baths are continuously sampled and periodically automatically analyzed; however, it will be appreciated that the invention may be used for analysis of only one bath.

Figures 1, 2:
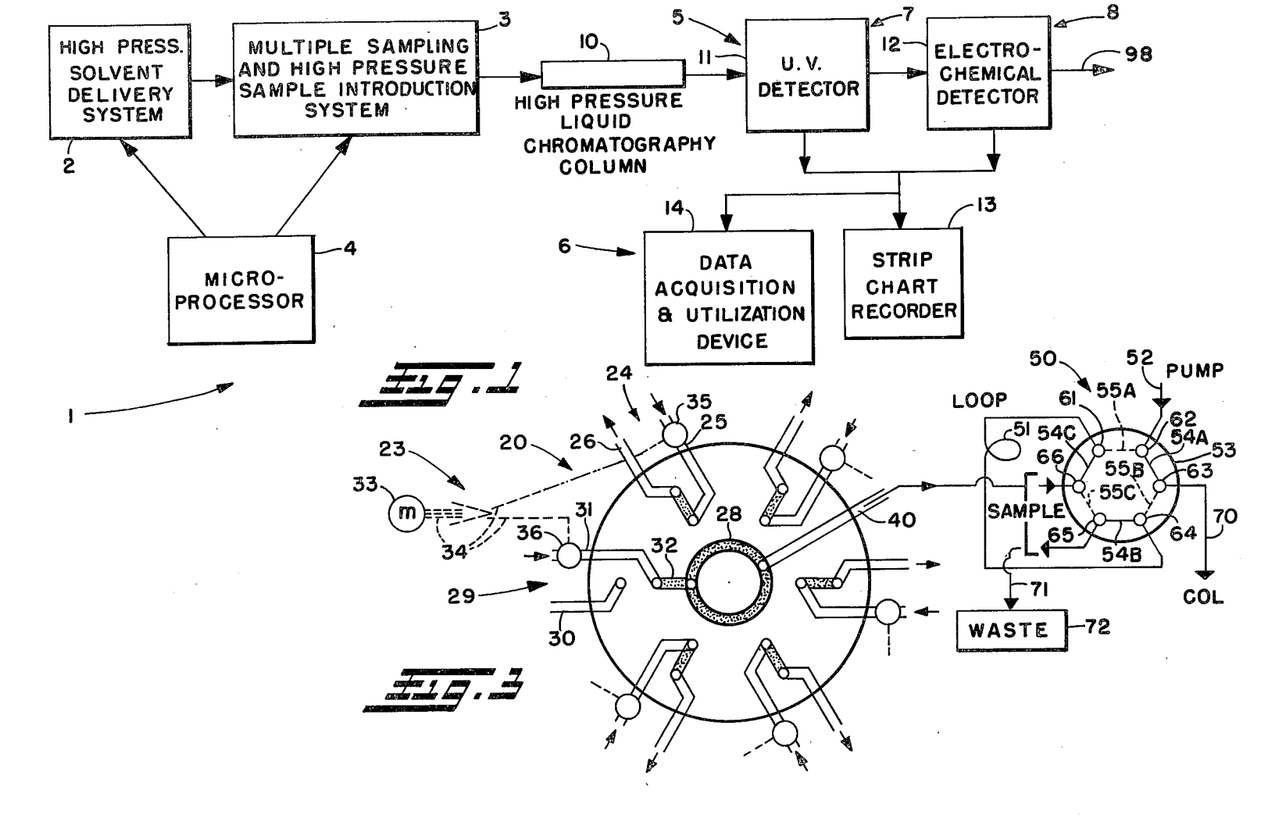
FIG. 1 is a block diagram of an analyzer for liquid solutions, and particularly for electroplating baths, in accordance with the present invention.
FIG. 2 is a schematic fluid and electrical diagram, partly in block form, of the analyzer of FIG. 1.
Figure 2:
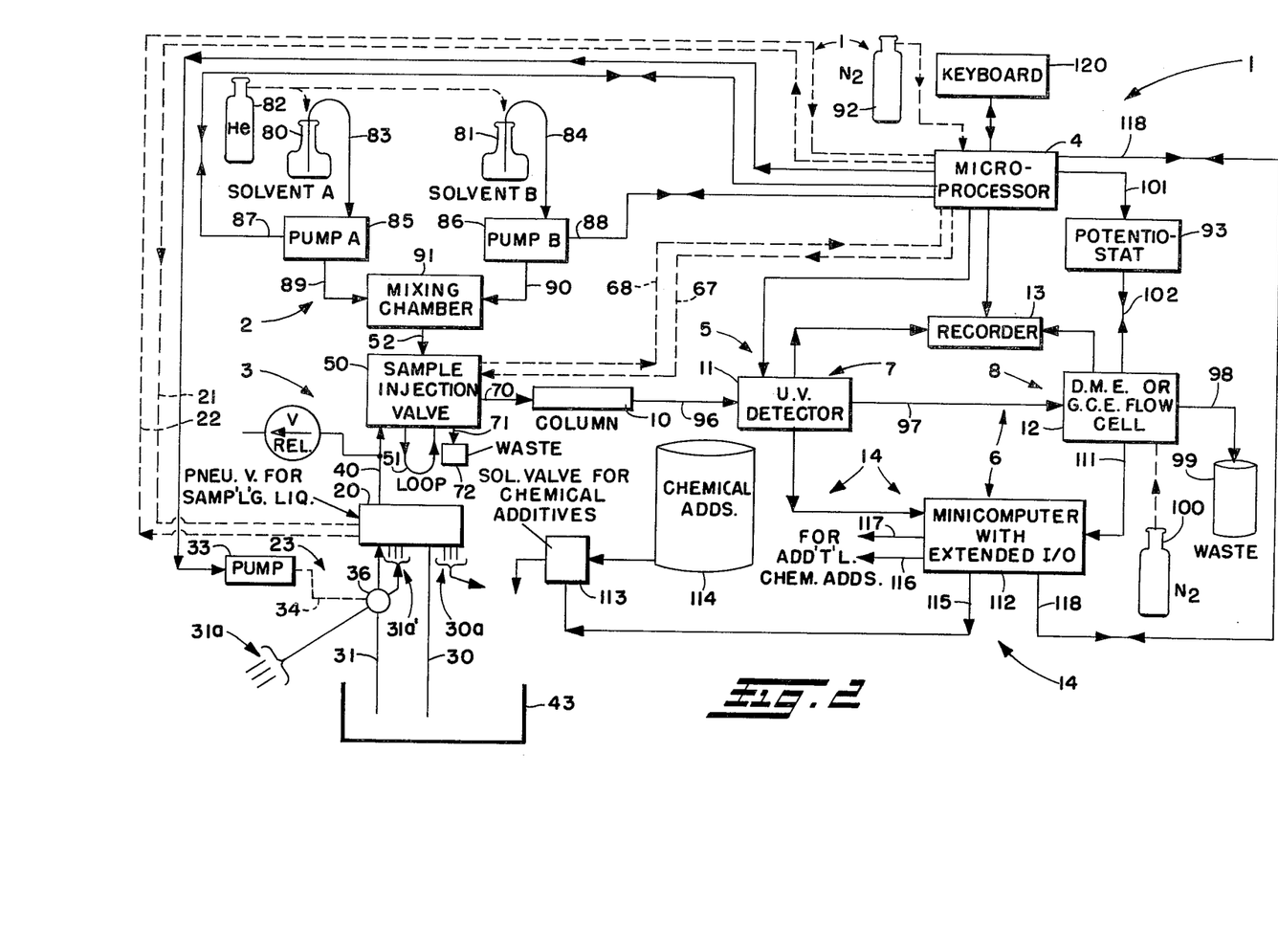

Referring now in detail to the drawings, wherein like reference numerals designate like parts in the several figures, and initially to FIG. 1, an analyzer for continuously sampling and periodically automatically analyzing plural electroplating baths is generally indicated at 1. The analyzer 1 includes a high pressure solvent delivery system 2, a multiple sampling and high pressure sample introduction system 3, both of which preferably are computer controlled, for example by a microprocessor controller 4, a detector system 5, and an information output device 6. Preferably the detector system 5 includes plural detector stages 7, 8 so that in the event that one detector stage is incapable of detecting a particular component of a sample, the other detector stage may be able to detect that component. In the preferred embodiment and best mode, prior to or upstream of the first detector stage 7 is a high pressure liquid chromatography (HPLC) column 10 and such first stage includes a spectrophotometric type detector, most preferably an ultraviolet electromagnetic radiation detector 11; and the second detector stage 8 is an electro-chemical detector 12, such as a commercially available polarograph type instrument which ordinarily is equipped with a flow cell. The information output device 6 preferably includes a multi-channel strip chart recorder 13 which displays output information from the respective detectors 11, 12 integrated with respect to time, as the chart paper is moved through the recorder; and a data acquisition and utilization device 14, which may include an electronic data manipulation and/or storage mechanism for storing information from the detectors as well as a further control mechanism for controlling a parameter of respective analyzed baths. For example, the data acquisition and utilization device 14 may include a minicomputer which controls one or more valves that provide additives to a bath to maintain the chemical nature of the latter within predetermined tolerances; the device 14 may control other parameters of the bath, such as temperature thereof, or may control external equipment, such as a shut-down mechanism or feed equipment that feed product into the bath for electroplating purposes based on the analysis information obtained by the analyzer 1.

Turning particularly to FIG. 2, the analyzer 1 is illustrated in greater detail. In achieving the objective of the analyzer 1, namely the analysis of respective liquid samples from electroplating baths, the individual samples are obtained at relatively low pressure and are combined with and pumped with one or more solvents at relatively high pressure through the HPLC column 10 to the first detector stage 7. The actual solvent material that flows through the detector system 5 will be referred to hereafter as the mobile phase. An aliquot of sample from a process bath mixed with and pumped with solvent, for example, is affected by the packing of the HPLC column 10 and is examined by the respective ultraviolet and polarographic type detectors 11, 12. The high pressure at which the solvents and the aliquot are pumped is necessary due to the resistance to flow of the HPLC column 10. The analyzer 1 is versatile in several respects, including the ability to analyze samples from plural electroplating baths, to effect such analysis using plural detectors which use different detection techniques, and to use one or more solvents individually with a sample to make an aliquot or mobile phase and/or to use various combinations of solvents at adjustably controlled percentages for the same.

To monitor periodically and automatically several processes, i.e. several electroplating baths, which are not at exceptionally low pressures or at high or low temperatures and which are occurring in solution, plural flow streams of liquid are taken, one from each monitored bath, and a single sample selection valve 20 that is controlled by the microprocessor 4 is employed to switch process streams, i.e. selectively to deliver a respective stream for analysis. The valve 20 preferably operates or switches in response to pneumatic signals on pneumatic lines 21, 22, which are coupled to the microprocessor controller 4. Thus, the microprocessor controller 4 may be, for example, an Altex Model 420 Microprocessor Control, which includes a microprocessor integrated circuit and associated support circuitry, memory circuitry, etc. and pneumatic input and output lines controlled thereby. Such pneumatic operation of the valve 20 provides reliable control thereof. Directly associated with the valve 20 is a peristaltic pump 23, such as a Buchler multiple vane, e.g. a 4-vane, 8-vane, or the like, multistatic pump. Moreover, the valve 20 preferably is a Valco Model AHCSF 4-HPA (the digit 4 represents the number of streams and in the preferred embodiment and best mode would be a digit 8 to indicate 8 streams) Stream Valve of Hastalloy C material together with a multiple way, 4-way, 8-way, etc., depending on the number of streams, air switch for operating the valve in response to the pneumatic signals on lines 21, 22 from the microprocessor controller 4.

Referring briefly to FIG. 3, the sample selection valve 20 and the peristaltic pump 23 are schematically illustrated. For convenience of illustration the valve 20 in FIG. 3 has only six flow channels, such as the channel 24, which has an inlet flow path 25, an outlet flow path 26, and a flow path completing mechanism or valving mechanism 27. The valving mechanism 27 may be operated selectively in response to pneumatic signals from the microprocessor controller 4 to complete or to interrupt the fluid connection between paths 25, 26 and in the latter condition importantly to connect the inlet flow path 25 with a common flow channel 28. Such a connection is illustrated in the sampling channel 29 in which the outlet flow path 30 is disconnected from the inlet flow path 31 and the latter is connected by the valving mechanism 32 to the common flow channel 28. All of the valving mechanisms, such as 27, 32, may be considered a flow selector of the valve 20. Preferably each of the respective inlet flow paths, such as 25, 31, is connected directly to a respective electroplating bath, the liquid of which is to be automatically analyzed periodically or to a reference source of liquid having concentrations of components, e.g. nickel, tin, copper, and associated organic and inorganic addition agents, against which those of the baths are to be compared; additionally, each outlet flow path, such as 26, 30, is connected directly back to the bath or source to which the associated inlet flow path, such as 25, 31, is connected. The pump 23 may include, for example, a constant speed electric motor 33 with an output shaft 34 on which are mounted plural pumping peristaltic cams, such as at 35, 36, for common rotation by the shaft 34 to pump fluid in the respective channels, suh as 24, 29. Accordingly, the inlet flow path, such as 25, 31, of each channel may include a flexible portion that is cooperative with a respective cam, such as 35, 36, to provide peristaltic pumping action in the respective channels. In FIG. 2 lines 31a represent other inlet flow paths from other baths, not shown, coupled to the respective pump cams and via lines 31a' to the valve 20; and lines 30a represent other respective outlet flow paths of respective flow channels for returning respective streams to their sources.

Thus, when a respective valving mechanism, such as 27, is closed to complete a flow path between the inlet and outlet flow paths 25, 26 of a given channel, liquid from the electroplating bath into which the flow path 25 extends is pumped through the channel and back via the outlet flow path 26 into the same electroplating bath to provide a continuous flow stream accurately representative of the present conditions, including, particularly, the chemical concentrations of the respective electroplating bath. However, when a respective valving mechanism or flow selector, such as at 32, is operated in the valve 20 to disrupt the connection with the outlet flow path 30 and to connect the inlet flow path 31 with the common flow channel 28, liquid from the electroplating bath flowing in the channel 29 is obtained and directed through an outlet channel 40 of the valve 20 for subsequent analysis. Accordingly, not only are the flow streams continuously flowing in the respective baths, but also the sample that is to be analyzed by the analyzer 1 is an on-stream sample which accurately represents the present conditions in the bath which will be analyzed as will be described in further detail below.

Turning back to FIG. 2, fluid intake and output fitting 41, 42 associated with the inlet and outlet flow paths 31, 30 for drawing liquid from and returning liquid to an electroplating bath 43 are illustrated. For convenience of illustration the additional flow channels of the valve 20 are not seen in FIG. 2. There are, of course, several advantages to using the described peristaltic pump 23. For example, plural streams may be pumped independently of each other in a convenient manner. Moreover, the interruption of a supply of liquid to the inlet fitting 41 or a blockage of a portion of the flow path downstream of the peristaltic cam, such as 36, will not adversely affect the pump or cause too high pressure in a flow line, and, therefore, ordinarily would not require a shut-down of the analyzer 1 while the pump 23 continues to pump liquid in the flow streams of the other channels of the valve 20. Moreover, the action of the peristaltic pump 23 preferably is relatively gradual so that the liquid flowing in the respective channels is not moving at high velocity nor is any undesirable turbulence created in the bath 43 by the small amount of liquid flowing through the respective flow channel associated therewith. Alternatively, other pumps may be used.

Use of such a described sample selection valve 20 minimizes the time lag between that at which a sample is drawn from a bath 43 and that at which analysis of the sample is made. When a particular process or bath is not being analyzed, the valve 20 is appropriately actuated so that the sample stream therefrom is returned to the process tank; whereas, when a process is to be analyzed, the valve 20 is properly actuated by the microprocessor controller 4 to direct the sample stream to a high pressure sample injection valve 50. Moreover, it will be appreciated that the valve 20 may be manufactured at relatively minimum cost since the liquids flowing therein are at relatively low pressure, with high pressure liquids being limited only to the sample injection valve 50 and those portions of the analyzer fluidically downstream of such valve.

The high pressure sample injection valve 50 may be a Rheodyne Model 7120 Syringe Loading Sample Injector which is modified to operate as a loop injector; such loop 51 has a fixed volume, for example on the order of one or several microliters, to obtain a known volume of liquid sample for analysis. The sample injection valve 50 is positioned between the sample selection valve 20 and the high pressure liquid chromatographic column 10. It is the purpose of the injection valve 50 both to obtain a known quantity of relatively uncontaminated liquid for analysis and to combine such quantity of liquid with a solvent liquid received from a solvent input line 52 for subsequent high pressure analysis.

The sample injection valve 50 is schematically illustrated in FIG. 3 including a valve housing 53 with a first group of flow paths 54A, B, C and a second group of flow paths 55A, B, C as well as a series of fluid ports 61–66. The sample injection valve 50 has two operational modes or positions directly controlled by pneumatic signals on lines 67, 68 from the microprocessor controller 4. In the load position, the first group of flow paths 54A, B, C conduct fluid. Thus, the mobile phase is simply the solvent received in the solvent input line 52, and that mobile phase flows through the port 62, flow path 54A, port 63, and analysis flow line 70 continuously to the HPLC column 10; and simultaneously the flow stream from channel 29 flows through the sample selection valve 20 through the outlet channel 40 to port 66 and from the latter via flow path 54C, port 61, loop 51, port 64, flow path 54B, port 65, and waste line 71 to a waste container 72. Thus, the sample loop 51 is continuously being filled with representative samples from the process tank electroplating bath 43.

In the second or sample inject position of the sample injection valve 50, fluid connections are effected only through the second group of flow paths 55A, B, C. In this position the flow of mobile phase solvent from solvent input line 52 and port 62 is directed through flow path 55A and port 61 through the loop 51 which contains the representative sample for analysis to form an aliquot therewith. The aliquot then flows to the HPLC column 10 (FIG. 2). In this manner a representative sample from the process tank 43 is volumetrically applied to the HPLC column 10.

With accurate control of the sample injection valve 50 by the microprocessor controller 4, and coordinated activity by the latter of the sample selection valve 20, so that the stream flowing through the outlet channel 40 is switched in time for the loop 51 to be loaded with a representative process tank sample before injection and then injected, say every hour, a process may be periodically monitored automatically and substantially continuously, i.e. every hour as opposed to once per day.

The high pressure solvent delivery system 2 has available two sources 80, 81 of solvents A, B, one of which may be water, that may be individually delivered to the solvent input line 52 or may be mixed in predetermined proportions prior to delivery to the line 52. The convenient availability of plural solvents, in this case two, but it will be appreciated that more than two may be used, if desired, further increases the over-all versatility of the analyzer 1. In the solvent delivery system 2 a source 82 of inert gas, such as helium, pressurizes the solvent sources 80, 81 to purge or degas the solvents of oxygen prior to delivery by tubes 83, 84 to individual high pressure pumps 85, 86. The pumps 85, 86 may be Altex Model 110 Solvent Metering Pumps, which are electronically controlled by signals on lines 87, 88 from the microprocessor controller 4, that produce an output flow in output lines 89, 90 at from about one to about five ml. per minute, preferably at about 2 ml. per minute, and at a pressure of from about 1000 to about 10,000 psi, usually about 2000 psi, generally in dependence on the characteristics of the column 10 and solvent flow rate, delivered to a mixing chamber 91, which may be a conventional high pressure solvent mixing chamber manufactured by Altex. Thus, depending on the electrical signals on lines 87, 88 from the microprocessor 4, the amount of solvent liquids pumped by the pumps 85, 86 will be controlled so that the solvent in solvent input line 52 for delivery to the sample injection valve 50 may be either solvent individually or a mixture of the solvents in proportions controlled by the microprocessor controller.

The microprocessor controller 4 accordingly provides a plurality of functions, as aforesaid, as well as additional functions to be described below in connection with the detector system 5 and information output device 6. Thus, the microprocessor controller 4 must be able to keep track of time with good precision; it should be able to control the high pressure pumps 85, 86 so that they provide a constant flow; it should be able to control the mobile phase solvent mixtures; it should actuate the sample selection valve 20 at specified time intervals, for example by controlling delivery of a pneumatic fluid such as inert nitrogen 92, through the pneumatic lines 21, 22; it must actuate the high pressure sample injection valve 50 by controlling the supply of pneumatic fluid to lines 67, 68 at specified time intervals; and, optionally, it can turn on and off a variety of devices, including, for example, the high pressure pumps 85, 86, the peristaltic pump 33, the detectors in the detector system 5, and the recorder 13, and it may signal the beginning of an event, such as sample injection, for the recorder 13, for another recorder in the data acquisition and utilization device 14, another microprocessor or computer associated with the device 14, etc.

In the detector system 5 there are plural detector stages, in the preferred embodiment two detector stages 7, 8. Preferably the detector stages are selected to complement each other so that those components of an electroplating bath which ordinarily may not be detected by one of the detector stages may be detected by the other one. Moreover, by placing the detector stages in fluid serial flow through relation and using at the input to the upstream detector a separation mechanism, such as a HPLC column 10, that affects or separates the sample flowing therethrough, such affectation may be utilized to facilitate analysis of samples by both detectors.

In the preferred embodiment and best mode of the invention the detector stage 7 is a spectrophotometric detector or other optical type detector or like detector that will not affect the aliquot, and most preferably is an ultraviolet electromagnetic radiation detector 11. The detector stage 8 is an electrochemical detector 12 which uses a polarography, differential polarography, or normal pulse polarography type analytical technique depending on electrical voltage signals delivered thereto by a potentiostat 93, as controlled by the microprocessor controller 4.

The characteristics of an HPLC column 10 are well known, for example, as described in *Liquid Chromatography in Practice,* P.A. Bristow (H. Oldfield & Son, Ltd., Macclesfield, United Kingdom, 1976). In the present invention, the HPLC column 10 must have a solid phase or liquid-solid phase, as is well known, which competes for the "affinity" of sample molecules in the mobile phase. The competition for this "affinity" between solid and mobile phases causes sample molecules to be delayed in their elution from the downstream end of the column and thus separation occurs. For the most part, a solid phase of bonded octyldecyl silane is sufficient in the chromatographic separations. The mobile phase may vary in concentration of two or more components from sample type to sample type. Therefore, if desired, the HPLC column 10 may actually comprise several parallel columns with a high pressure column switching valve between the sample injection valve 50 and the respective columns to select the individual column through which respective samples may flow; each column, of course, would have a different packing material. However, it is delivered that even though a process may vary greatly in application, for example gold electroplating and nickel electroplating, the similarities in the process, such as water solubility, make column selection less critical than proper mobile phase selection. Therefore, the high pressure solvent delivery system 2 may be accurately controlled to assure consistent, yet selectively changeable, mobile phase compositions so that switching of HPLC columns ordinarily will be unnecessary.

A wide variety of ultraviolet electromagnetic radiation detectors has been used in connection with liquid chromatography, as is described, for example, in the Bristow text. If a solvent is used that absorbs little or no ultraviolet radiation at a specified wavelength, say between 190 nm. and 350 nm., and a component of a process does absorb radiation at that wavelength, the difference in absorption is proportional to the concentration of the component. The magnitudes of such absorptions can be detected in conventional manner by the detector 11 and signals representative of absorption can be delivered on lines 94 to the recorder 13. By integrating the absorption information versus the flow of the mobile phase, an accurate concentration of the component relative to other components or relative to a standard may be obtained. The recorder 13, which preferably is a strip chart recorder, facilitates such integration by recording absorbance continuously while the chart paper moves at a fixed rate, which is in effect directly proportional to the flow rate of the mobile phase through the column 10 and detector 11. Therefore, as a component passes through the detector 11 a peak of absorbance versus time or volume, as flow rate, if constant, is proportional to time, is recorded. The area under the peak, then, is proportional to concentration of that component. If desired, of course, other types of recorders and/or integrators may be used.

Although all components of a process may not absorb ultraviolet radiation, a large variety of organic molecules, all metallic ions, and most anions may affect the current being evolved between two electrodes kept at a known potential or pulsed at regular voltage steps. The electrochemical detector 12, which may be one sold by Princeton Applied Research, Model 303, Dropping Mercury Electrode System with a flow cell adapter in combination with the potentiostat voltage supply source 93, such as a Princeton Applied Research Model 364 polarographic analyzer, which delivers a controlled voltage to the electrodes of the detector 12. If a mobile phase solvent is being passed between the electrodes of the detector 12, which are located in a conventional flow cell, a constant amperage due to reduction or oxidation of the solvent at the working electrode, which is preferably a glassy carbon electrode (G.C.E.) or a dropping mercury electrode (D.M.E.), is present. This amperage is subject to radical changes if a component passes the working electrode that is oxidized or reduced. The change in current at the working electrode is, as in the case of the ultraviolet radiation absorption, proportional to the concentration of the component being oxidized or reduced, although such a proportional relation may not necessarily be a linear one. In electroplating solutions, all metal ions that can be reduced and all active brightener components affect reduction at the cathode. Therefore, the electrochemical detector 12 is particularly useful for analysis and/or control of electroplating solutions. The output information from the electrochemical detector 12 may be delivered via line 95 to the recorder 13 for handling, i.e. recording and effective integration, essentially in the same manner that the data from the ultraviolet detector 11 is handled by the recorder 13.

During analysis of the mobile phase flowing through the detector system 5, then, such mobile phase flows through the HPLC column 10, flow line 96, ultraviolet detector 11, flow line 97, the flow cell of the electrochemical detector 12, and flow line 98 to a waste receptacle 99. A source of inert gas 100, such as nitrogen, may be connected to the electrochemical detector 12 for normal purposes, such as purging, reference signal generation, etc. Moreover, the microprocessor controller 4 may provide control signals via line 100 to control the wavelength at which the ultraviolet radiation detector 11 operates to provide further versatility for the analyzer 1. Additionally, the microprocessor controller 4 may provide electrical control signals on line 101 to cause the potentiostat 93 to vary the voltage delivered and fed back on lines 102 with respect to the electrochemical detector 12 during operation of the latter to utilize the various analytical techniques of, for example, polarography, differential polarography, or normal pulse polarography. Further, it will be appreciated that varying the operational wavelength of the ultraviolet detector 11 and/or the voltage at which the electrochemical detector 12 operates during an analytical run may help to detect the concentration of components that could not be analyzed at other wavelengths or voltages; however, in the preferred embodiment and best mode, ordinarily such variations would not be used.

Data acquisition from the detector system 5 may be effected by means other than a strip chart recorder 13. In particular, the data acquisition and utilization device 14 may be coupled by lines 110, 111 to receive electrical signals from the ultraviolet and electrochemical detectors 11, 12 and may include, for example, a computer that can integrate the peak area electronically and recognize individual peaks by their elution volume. Such computer may comprise part of the microprocessor controller 4 or may be a separate computer, such as a minicomputer 112, which may be a Hewlett-Packard Model 9125 minicomputer. Such computer 112 may also be programmed to activate pumps, not shown, valves, such as valve 113, to add chemical additives, say from a storage tank 114, to the process tank based on the analysis made by the analyzer 1 of that particular process tank, e.g. process tank or bath 43, etc. Preferably the valve 113 is an electrically responsive one that will fail only in a closed position and requires an affirmative signal to open. The computer 112 may have several output lines 115, 116, 117, etc. for controlling respective chemical additives for a single bath, for plural baths, etc. Moreover, a tie-in bus 118 provides interconnection between the microprocessor controller 4 and the computer 112 for coordinated operation thereof. It will be appreciated that a single computer, such as a minicomputer or a microprocessor controller having adequate capacity, may be substituted for the microprocessor 4 and computer 112 to effect the functional operations thereof.

It also will be appreciated that the computer 112 may effect other control functions with respect to the process bath 43, such as, for example, controlling temperature thereof, the speed with which product is passed therethrough, the amount of product passed therethrough for electroplating purposes, shut-down of an electroplating process, as well as the addition of chemicals thereto.

Exemplary operation of an analyzer in accordance with the present invention is presented in two examples below.

EXAMPLE 1

A liquid for an electroplating bath is analyzed. A 20 minute automatically repeatable cycle of operation of the analyzer 1 is programmed into the microprocessor 4 via the keyboard 120 associated therewith. For the initial condition, i.e. prior to time zero, a continuous stream of electroplating solution is being pumped via line 31 and pump 23 to the sample injection valve 50, through the sample loop 51 and back to the plating solution so that the sample loop is filled with refreshed representative solution ready for analysis. At time zero, i.e. at the start of the cycle, a mixture of solvents from sources 80, 81 is pumped by pumps 85, 86 and mixed in mixing chamber 91 for delivery via the solvent input line 52 to the sample injection valve 50; also at time zero the sample injection valve 50 is operated to the inject position so that such solvent mixture is pumped through the sample loop 51 to mix with the sample therein and to pump the same through the detector system 5 for analysis thereby, as aforesaid. At one minute into the cycle the sample injection valve 50 is switched to the load position so that shortly thereafter only the solvent mixture continues to pass through the detector system 5. At fifteen minutes into the cycle the proportions of solvents delivered to the sample injection valve 50 commences to change gradually over a following two minute time period so that the solvent mixture delivered to the sample injection valve thereafter is exclusively the solvent B contained in source 81. At nineteen minutes into the cycle an alarm, not shown, is energized to indicate that the end of that cycle and, more importantly, the beginning of the next cycle, is approaching in one minute. At twenty minutes into the cycle, the program returns to time zero, whereupon the program repeats effectively to obtain injection of a sample into the mobile phase analyzed by the detector system 5.

Moreover, preferably at the beginning of each cycle, i.e. at time zero, the proportions of the two solvents delivered to and mixed in the mixing chamber changes gradually so that for the first ten minutes of the cycle the mixture in line 52 will gradually change from 100% of solvent B to equal proportions of solvents A and B. During the entire analysis process the detector system 5 provides output information particularly at the recorder 13 which provides graphical output information indicative of the concentrations of the materials flowing through the detector system 5.

EXAMPLE 2

The ultraviolet detector 11, electrochemical detector 12, peristaltic pump 33 and microprocessor controller 4 are all on. Representative streams (lag time less than two minutes) are being pumped continuously through a 16-port (8 sample stream) sample selection valve 20. The solvent A in the system is water, and the other solvent B source 81 is acetonitrile ($CH_3CN$). The sample selection valve 20 is directing sample from a water reservoir, not shown, through the sample loop 51 of injection valve 50 which is in the load position to keep the valve clean. The sequence of events occurring over a one hour (from Time 0 minutes to Time 60 minutes) is, as follows:

| Time | |
|---|---|
| 0 | High pressure pumps 85, 86 are started at a combined flow = 2 milliliter/minute; the mobile phase composition in line 52 is adjusted to 20% $CH_3CN$ (solvent A is 80% and solvent B is 20% of the combined flow); recorder 13 turned on; sample selection valve 26 is rotated to a nickle standard stream, not shown, containing nickel and nickel salts and associated organic and inorganic additives in aqueous solution at a predetermined desired concentration. |
| 2 | Sample injection valve 50 switched to inject; signal to recorder 13 to record analyzed information (the signals to the recorder mentioned below also effect recording of information for at least the time period that valuable analysis information would be expected from the detector system). |
| 2.2 | Sample injection valve 50 switched to load. |
| 2.3 | Sample selection valve 20 switched to nickel plating bath stream, say from bath 43. |
| 8 | All components of the nickel standard sample have been separated, analyzed and recorded; sample injection valve 50 switched to inject; signal to recorder 13. |
| 8.2 | Sample injection valve 50 switched to load; sample selection valve 20 switched to water. |
| 10 | Sample selection valve switched to Copper Standard. |
| 13 | All components of the nickel plating bath have been separated and recorded; solvent composition changed to 50% $CH_3CN$ (it takes 5 minutes for this to equilibrate). |
| 25 | Sample injection valve switched to inject; signal to recorder 13. |
| 25.2 | Sample injection valve switched to load; sample selection valve switched to copper plating bath stream. |
| 30 | All copper standard components have been separated and recorded; sample injection valve switched to inject; signal to recorder 13; sample selection valve changed to water. |
| 30.2 | Sample injection valve switched to load. |
| 32 | Sample selection valve changed to tin standard. |
| 35 | All copper plating bath components have been analyzed and recorded; sample injection valve switched to inject; signal to recorder 13. |
| 35.2 | Sample injection valve switched to load. |
| 40 | All tin components have been separated and recorded; sample injection valve switched to inject; signal to recorder 13. |
| 40.2 | Sample injection valve switched to load; sample selection valve |

| Time | |
|---|---|
| | switched to water. |
| 45 | All tin plating bath components have been separated and recorded; mobile phase composition changed to 20% CH$_3$CN (this takes 5 minutes for equilibration). |
| 50 | High pressure pumps off(flow = 0), recorder off. |
| 60 | Start sequence again at 0. |

In view of the foregoing it will be appreciated that the analyzer 1 may be used effectively to analyze electroplating baths and other liquids, solutions, mixtures, etc. and, if desired, to provide automatic control of the monitored process.

What is claimed is:

1. An on-stream analyzer for liquid solutions, mixtures, and the like comprising supply means for supplying a stream of such liquid at a relatively low pressure, selecting means for selecting a sample of such stream of liquid for analysis, separating means for high pressure separation of components of such sample, detector means for detecting the concentration of at least one component of such sample, and pressurizing means for delivering such sample at relatively high pressure to said separating means for relatively high pressure separation thereby, said separating means comprising high pressure liquid chromatography means for passing such sample therethrough while retarding the passage of at least one of the components of such sample relative to passage of another component of such sample, and said detector means comprising first detector means fluidically downstream of said separating means for detecting the concentration of at least one component in such sample, and second detector means fluidically downstream of said first detector means for detecting the concentration of at least another component in such sample.

2. The analyzer of claim 1, said supply means comprising means for supplying at least one stream of liquid from at least one electroplating bath and said detector means comprising means for detecting the concentration of at least one component of such liquid as an indication of the concentration of such component in such electroplating bath.

3. The analyzer of claim 1, wherein said supply means and said stream selection means provide such streams at relatively low pressure, and said sample obtaining means comprises means for pressurizing such sample to relatively high pressure.

4. The analyzer of claim 58 further comprising solvent delivery means for delivering at least two solvents selectively to transport such sample to and through said detector means, and control means for controlling delivery of said respective solvents and, thus, the proportions of each used to transport such sample.

5. The analyzer of claim 4, further comprising high pressure pump means for controllably delivering said respective solvents at high pressure relative to that of such sample thereby to increase the pressure of the latter for high pressure analysis thereof.

6. The analyzer of claim 1, said first detector means comprising means for detecting ultraviolet radiation absorption, and said second detector means comprising an electrochemical detector.

7. The analyzer of claim 6, said electrochemical detector comprising a polarograph type detector.

8. The analyzer of claim 1, said pressurizing means comprising a valve assembly, high pressure solvent delivery means for delivering solvent to said valve assembly, and said valve assembly including a first pair of flow path means operable when said valve assembly is in a load mode for passing such stream of liquid through a fixed volume flow path to provide a continuously refreshed sample therein and for simultaneously passing a stream of solvent to said detector means, and a second pair of flow path means operative when said valve assembly is in an inject mode for passing such selected stream through said valve assembly bypassing said fixed volume flow path while leaving such sample therein and for passing such stream of high pressure solvent to said fixed volume flow path for transporting such sample therein to said detector means.

9. An on-stream analyzer for electroplating baths, comprising supply means for supplying at least one stream of liquid from at least one bath, selecting means for selecting a stream of liquid from said supply means for analysis, and detector means for detecting the concentration of at least one component in a sample of such selected stream, said supply means comprising means for supplying separate flowing streams of liquid from plural respective baths, said selecting means comprising valve means for selecting individual respective streams for analysis, and said detector means comprising a first detector stage including a high pressure liquid chromatography column and an ultraviolet radiation detector and a second detector stage including an electrochemical detector fluidically coupled to and downstream of said first detector stage.

10. The analyzer of claim 1, 9, said supply means comprising a peristaltic pump.

11. The analyzer of claim 9, further comprising computer control means for automatically periodically selectively controlling said selecting means to direct each stream only one stream at a time for analysis.

12. The analyzer of claim 11, said valve means comprising a pneumatic actuated valve and said computer control means comprising microprocessor control means for controllably delivering pneumatic signals to said valve selectively to actuate said respective flow selector means.

13. The analyzer of claim 9, further comprising sample injection valve means for obtaining respective measured volume samples from respective selected streams and injecting the same into said high pressure liquid chromatography column.

14. The analyzer of claim 13, further comprising high pressure solvent delivery means for delivering solvent to said sample injection means, and said sample injection means comprising a first pair of flow path means operable when said sample injection means is in a load mode for passing the selected stream through a fixed volume flow path to provide a continuously refreshed sample therein and for simultaneously passing a stream of solvent to said detector means, and a second pair of flow path means operable when said sample injection means is in an inject mode for passing such selected stream through said sample injection means bypassing said fixed volume flow path while leaving such sample therein and for passing such stream of solvent to said fixed volume flow path for mixing with and/or transporting of such sample therein to said detector means.

15. The analyzer of claim 14, further comprising solvent delivery means for delivering at least two solvents selectively to transport such sample to and through said detector means, and control means for automatically periodically controlling delivery of said respective solvents and, thus, the proportions of each used to transport such sample.

16. The analyzer of claim 14, further comprising solvent delivery means for delivering at least two solvents at controlled proportions selectively to transport such sample to and through said detector means, and further comprising computer type control means for automatically periodically controllably operating said supply means, said selecting means, and said solvent delivery means to deliver respective individual samples in combination with controlled proportions of solvents in the solvent transport media to said detector means for analysis thereby.

17. An on-stream analyzer for electroplating baths, comprising supply means for supplying a plurality of streams of liquid, at least one from each of plural baths, selecting means for selecting one stream of liquid at a time from said supply means for analysis, separating means for passing such sample therethrough while retarding the passage of at least one of the components of such sample relative to passage of another component of such sample, and detector means for detecting the concentration of at least one component in a sample of such selected stream, said detector means including first detector means downstream of said separating means for detecting the concentration of at least one component in such sample, and second detector means fluidically downstream of said first detector means for detecting the concentration of at least another component in such sample.

18. The analyzer of claim 17, further comprising sample obtaining means for directing to said detector means a sample of liquid from such selected stream for analysis by said detector means, said sample obtaining means comprising first flow path means for passing such selected stream through a fixed volume, second flow path means for passing such selected stream through said sample obtaining means bypassing said fixed volume while leaving a sample of liquid from such selected stream in said fixed volume, and third flow path means for directing a further stream of fluid to said fixed volume to urge such sample of fluid therein through said sample obtaining means to said detector means, said sample obtaining means further comprising fourth flow path means for directing such further stream of liquid to said detector means and control means for selectively controlling said flow path means in a load mode to load liquid from such selected stream by flow thereof through said first flow path means and to direct such further stream of fluid through said fourth flow path means to said detector means or in an inject mode to direct such selected stream through said second flow path means and to direct such further stream of fluid through said third flow path means to transport such sample of fluid in said fixed volume to said detector means.

19. The analyzer of claim 18, said sample obtaining means further comprising a pneumatically operated valve and said control means comprising electronic control means for automatically periodically controllably delivering pneumatic signals to said valve.

20. The analyzer of claim 18, such further stream of fluid comprising a liquid solvent, and further comprising high pressure solvent delivery means for delivering such stream of solvent at a high pressure relative to that of such selected stream.

21. The analyzer of claim 21, said separating means comprising a high pressure liquid chromatography column means for separating components of such sample and said first detector means comprising a spectrophotometric electromagnetic detector means for examining the elution from said column means.

22. The analyzer of claim 21, said spectrophotometric detector means comprising an ultraviolet radiation detector fluidically downstream of said column means and said second detector means further comprising an electrochemical detector fluidically downstream of said ultraviolet radiation detector means.

23. The analyzer of claim 22, further comprising output means for integrating, recording and displaying information concerning the concentrations detected by said detector means.

24. The analyzer of claim 23, said output means comprising a strip chart recorder.

25. The analyzer of claim 22, further comprising parameter control means responsive to the concentration information detected by said detector means for controlling a parameter of the bath from which the analyzed sample was derived.

26. The analyzer of claim 17, said supply means comprising peristaltic pump means for pumping fluid of each stream through said selecting means.

27. The analyzer of claim 17, further comprising parameter control means responsive to the concentration information detected by said detector means for controlling a parameter of the bath from which the analyzed sample was derived.

28. The analyzer of claim 27, said parameter control means comprising means for controllably delivering chemical additives to such bath to maintain selected chemical concentrations thereof within predetermined tolerances, and further comprising computer control means for controlling said means for controllably delivering in response to the concentration information.

29. The analyzer of claim 17, further comprising computer type control means for automatically periodically controllably operating said supply means and said selecting means to deliver respective individual samples to said detector means for analysis thereby.

* * * * *

UNITED STATES PATENT AND TRADEMARK OFFICE
CERTIFICATE OF CORRECTION

PATENT NO. : 4,326,940

DATED : April 27, 1982

INVENTOR(S) : William E. Eckles; Craig V. Bishop; and Peter T. Vaitekunas

It is certified that error appears in the above—identified patent and that said Letters Patent is hereby corrected as shown below:

In the Abstract:

Line 10, correct "multi-steam" to read --multi-stream--; and in lines 10 and 11, correct "value" to read --valve--.

Signed and Sealed this

Eighth Day of September, 1987

Attest:

DONALD J. QUIGG

Attesting Officer

Commissioner of Patents and Trademarks